US006835750B1

(12) United States Patent
Henderson (10) Patent No.: US 6,835,750 B1
(45) Date of Patent: Dec. 28, 2004

(54) USE OF MEDIUM CHAIN TRIGLYCERIDES FOR THE TREATMENT AND PREVENTION OF ALZHEIMER'S DISEASE AND OTHER DISEASES RESULTING FROM REDUCED NEURONAL METABOLISM II

(75) Inventor: Samuel T. Henderson, Broomfield, CO (US)

(73) Assignee: Accera, Inc., Broomfield ( * ) Notice: Subject to any disclaimer, the term of this patent is extended or adjusted under 35 U.S.C. 154(b) by 19 days.

(21) Appl. No.: 10/152,147

(22) Filed: May 20, 2002

Related U.S. Application Data (63) Continuation-in-part of application No. 09/845,741, filed on May 1, 2001.
(60) Provisional application No. 60/375,909, filed on Apr. 26, 2002, and provisional application No. 60/200,980, filed on May 1, 2000.

(51) Int. Cl.$^7$ ...................... A61K 31/19; A61K 31/225; A61K 31/20; A61K 31/185
(52) U.S. Cl. ...................... 514/557; 514/547; 514/560; 514/578
(58) Field of Search ................................ 514/547, 557, 514/573, 560

(56) References Cited

U.S. PATENT DOCUMENTS

| | | | |
|---|---|---|---|
| 4,407,821 A | | 10/1983 | Mendy |
| 4,528,197 A | * | 7/1985 | Blackburn |
| 4,847,296 A | | 7/1989 | Babayan et al. |
| 5,385,915 A | | 1/1995 | Buxbaum et al. |
| 5,391,375 A | | 2/1995 | Hille et al. |
| 5,504,072 A | | 4/1996 | Schmidt et al. |
| 5,538,983 A | | 7/1996 | Buxbaum et al. |
| 5,650,148 A | | 7/1997 | Gage et al. |
| 5,817,626 A | | 10/1998 | Findeis et al. |
| 5,854,204 A | | 12/1998 | Findeis et al. |
| 5,854,215 A | | 12/1998 | Findeis et al. |
| 5,925,684 A | | 7/1999 | Schweikert et al. |
| 5,936,078 A | | 8/1999 | Kuga et al. |
| 5,980,939 A | | 11/1999 | Kim et al. |
| 6,136,862 A | | 10/2000 | Hiraide et al. |
| 6,207,856 B1 | | 3/2001 | Veech |
| 6,232,345 B1 | | 5/2001 | Hiraide et al. |
| 6,395,306 B1 | | 5/2002 | Cui et al. |

FOREIGN PATENT DOCUMENTS

| | | |
|---|---|---|
| JP | 6-287138 | 6/1994 |
| WO | WO 96/14063 | 5/1996 |
| WO | WO 98/41200 | 9/1998 |
| WO | WO 98/41201 | 9/1998 |
| WO | WO 99/51097 | 10/1999 |
| WO | WO 00/15216 | 3/2000 |

OTHER PUBLICATIONS

Beffert et al. (1998) Brain Research Reviews 27:119–142.
Blass, J.P., and Zemcov, A. (1984) Neurochem Path. 2:103–14.
Craft et al. (1996) Neurobiology of Aging 17 (1):123–130.
Corbo et al. (1999) Ann. Hum. Genet. 63:301–310.
Davis et al. (1999) Nature 400:810.
Edmond (1992) Can. J. Physiol. Pharmacol. 70:S118–S129.
Evans et al. (1989) JAMA 262 (18):2551–2556.
Finch et al. (1997) Experimental Neurology 143:82–102.
Frölich et al. (1998) J. Neural Transm 105:423–438.
Goodman, L. S., Limbird, L. E., Milinoff, P. B., Gilman, A. G., and Hardman, J. G. (editors), (1996). The Pharmacological Basis of Therapeutics, 9.sup.th Ed., McGraw–Hill. Table of contents.
Gregg et al. (1996) The Journal of Clinical Investigation, Inc. 78:815–821.
Hall et al. (1998) Australian and New Zealand Journal of Psychiatry 32:698–706.
Hamosh, M. (1990) In: Lingual and Gastric Lipases: Their role in fat digestion. CRC press, Boca Raton, FL., Table of contents and relevant pages.
Hanlon et al. (1995) Atherosclerosis 112:85–90.
Hasselbalch et al. (1996) The American Physiological Society, Cerebral Metabolism and Blood Flow in Hyperketonemia, E746–E751.
Hoyer (1998) J. Neural Transm. 105:415–422.
Hoyer, S. (1992) Mol Chem Neuropathol 16:207–24.
Jolles et al. (1992) Journal of Neurochemistry 58 (6):2326–2329.
Kolanowski et al. (1994) Metabolism 43 (2):180–185.
Klivenyi et al. (1999) Nature Medicine 5 (3):347–350.
Koo et al. (1999) Proc. Natl. Acad. Sci. 96:9989–9990.
Knouff et al. (1999) The Journal of Clinical Investigation 103(11):1579–1586.
Lannert et al. (1998) Behavioral Neuroscience 112 (5):1199–1208.
Loktionov et al. (1999) Atherosclerosis 145:125–135.
Mattson (1998) Science and Medicine, Mar./Apr.: 17–25, Experimental Models of Alzheimer's Disease.
McKhann et al. (1984) Neurology 34:939–943.
Meier–Ruge et al. (1994) Gerontology 40:246–252.
Messier et al. (1996) Behavioural Brain Research 75:1–11.
Neve et al. (1998) Trends Neurosci. 21:15–19.
Nishimura et al. (1999) Clin. Genes 55:219–225.

(List continued on next page.)

Primary Examiner—Theodore J. Criares
(74) Attorney, Agent, or Firm—Swanson & Bratschun, L.L.C.

(57) ABSTRACT

Methods and compositions for treating or preventing, the occurrence of senile dementia of the Alzheimer's type, or other conditions arising from reduced neuronal metabolism and leading to lessened cognitive function are described. In a preferred embodiment the administration of triglycerides or fatty acids with chain lengths between 5 and 12, to said patient at a level to produce an improvement in cognitive ability.

4 Claims, 2 Drawing Sheets

OTHER PUBLICATIONS

Odle, J. (1997) J Nutr. 127:1061–1067.
Ogawa et al. (1996) J Neurol Sci 139:78–82.
Osuntokun et al (1995) Ann Neurol 38:463–465.
Reiman et al. (1996) N Engl J Med 334:752–758.
Roheim et al. (1979) Proc Natl Acad Sci U S A 76:4646–4649.
Selkoe, D. J. (1994) J. Neruopathol. Exp. Neruol. 53:438–447.
Selkoe, D. J., (1999) Nature Supplement 399:A23–31.
Simpson, I. A., and Davies, P. (1994) Ann Neurol 36:800–801.
Swaab, et al. (1998) Prog Brain Res 117:343–377.
Veneman et al. (1994) Diabetes 43:1311–1317.
Zekraoui et al. (1997) Hum Biol 69:575–581.
Zubenko et al. (1999) Biol Psychiatry 45:731–736.
Database CABA on STN, (Columbus, OH, USA), No. 991412046, Mak, S.C. et al 'Clinical experience of ketogenic diet on children with refractory epilepsy,' abstract, Acta Paediatrica Sinica, 1999, 40 (2), 97–100.

Database MEDLINE on STN (Columbus, OH, USA), No. 96063810, Bruno, G. et al. 'Acetyl–L–carnitine in Alzheimer disease: a short–term study on CSF neurotransmitters and neuropeptides,' abstract, Alzheimer Disease And Associated Disorders, Fall 1995, 9 (3), 128–31.

Mak et al. (1999) Acta. Paeditr Sin 40(2):97–100.

Patent Abstracts of Japan, Abstract for Publication No. 06–287138, (Sep. 22, 2003).

Dialog Results (Sep. 22, 2003) Agent for Prevention and/or therapeutics of Alzheimer's disease–contg. Triglyceride of 8–10 carbon fatty acids as active ingredient, Translation of Publication No. 06–287138.

Cox et al. (1998) J of Pediatrics 133(2):247–253.

Thal et al. (1996) Neurology 47(3):705–711.

Kashiwaya et al. (2000) Proc Natl Acad Sci USA 97(10):5440–5444.

* cited by examiner

USE OF MEDIUM CHAIN TRIGLYCERIDES FOR THE TREATMENT AND PREVENTION OF ALZHEIMER'S DISEASE AND OTHER DISEASES RESULTING FROM REDUCED NEURONAL METABOLISM II

CROSS REFERENCE TO RELATED APPLICATIONS

This application is a continuation-in-part of U.S. application Ser. No. 09/845,741, filed May 1, 2001, entitled "Use of Medium Chain Trigylcerides for the Treatment and Prevention of Alzheimer's Disease and Other Diseases Resulting from Reduced Neuronal Metabolism," which claims priority to U.S. Provisional Application Ser. No. 60/200,980 filed May 1, 2000, entitled "Use of Medium Chain Triglycerides for the Treatment and Prevention of Alzheimer's Disease and Other Diseases Resulting from Reduced Neuronal Metabolism." This application also claims the benefit of U.S. Provisional Application Ser. No. 60/375,909, filed Apr. 26, 2002, entitled "The Effect of Medium Chain Triglycerides on Memory in Mild Cognitive Impairment and Alzheimer's Disease."

FIELD OF THE INVENTION

This invention relates to the field of therapeutic agents for the treatment of Alzheimer's Disease, and other diseases associated with reduced neuronal metabolism, including Parkinson's disease, Huntington's Disease, and epilepsy.

BACKGROUND OF THE INVENTION

Alzheimer's Disease (AD) is a progressive neurodegenerative disorder, which primarily affects the elderly. There are two forms of AD, early-onset and late-onset. Early-onset AD is rare, strikes susceptible individuals as early as the third decade, and is frequently associated with mutations in a small set of genes. Late onset, or spontaneous, AD is common, strikes in the seventh or eighth decade, and is a mutifactorial disease with many genetic risk factors. Late-onset AD is the leading cause of dementia in persons over the age of 65. An estimated 7–10% of the American population over 65, and up to 40% of the American population greater than 80 years of age is afflicted with AD (McKhann et al., 1984; Evans et al. 1989). Early in the disease, patients experience loss of memory and orientation. As the disease progresses, additional cognitive functions become impaired, until the patient is completely incapacitated. Many theories have been proposed to describe the chain of events that give rise to AD, yet, at the time of this application, the cause remains unknown. Currently, no effective prevention or treatment exists for AD. The only drugs to treat AD on the market today, Aricept®, Cognex®, Reminyl® and Exelon® are acetylcholinesterase inhibitors. These drugs do not address the underlying pathology of AD. They merely enhance the effectiveness of those nerve cells still able to function and only provide symptomatic relief from the disease. Since the disease continues, the benefits of these treatments are slight.

Early-onset cases of AD are rare (~5%), occur before the age of 60 and are frequently associated with mutations in three genes, presenilinl (PS1), presenting (PS2) and amyloid precursor protein (APP) (for review see Selkoe, 1999). These early-onset AD cases exhibit cognitive decline and neuropathological lesions that are similar to those found in late-onset AD. AD is characterized by the accumulation of neurofibrillar tangles (NFT) and β-amyloid deposits in senile plaques (SP) and cerebral blood vessels. The main constituent of senile plaques is the β-amyloid peptide (Aβ), which is derived from the APP protein by proteolytic processing. The presenilin proteins may facilitate the cleavage of APP. The Aβ peptide is amyloidagenic and under certain conditions will form insoluble fibrils. However, the toxicity of Aβ peptide and fibrils remains controversial. In some cases Aβ has been shown to be neurotoxic, while others find it to be neurotrophic (for reviews see Selkoe, 1999). The cause of early-onset AD is hypothesized to be accumulation of aggregated proteins in susceptible neurons. Mutations in APP are hypothesized to lead to direct accumulation of fibrillar Aβ, while mutations in PS1 or PS2 are proposed to lead to indirect accumulation of Aβ. How a variety of mutations in PS1 and PS2 lead to increased AB accumulation has not been resolved. Accumulation of aggregated proteins is common to many progressive neurodegenerative disorders, including Amyloid Lateral Sclerosis (ALS) and Huntington's Disease (for review see Koo et al., 1999). Evidence suggests that accumulation of aggregated proteins inhibits cellular metabolism and ATP production. Consistent with this observation is the finding that buffering the energy capacity of neurons with creatine will delay the onset of ALS in transgenic mouse models (Klivenyi et al., 1999). Much of the prior art on AD has focused on inhibiting production of or aggregation of AB peptides; such as U.S. Pat. No. 5,817,626, U.S. Pat. No. 5,854,204, and U.S. Pat. No. 5,854,215. Other prior art to treat AD include, U.S. Pat. No. 5,385,915 "Treatment of amyloidosis associated with Alzheimer Disease using modulators of protein phosphorylation", patent U.S. Pat. No. 5,538,983, "Method of treating amyloidosis by modulation of calcium." Attempts to increase neuronal survival by use of nerve growth factors have dealt with either whole cell, gene or protein delivery, such as described in U.S. Pat. No. 5,650,148 "Method of grafting genetically modified cells to treat defects, disease or damage of the central nervous system", and U.S. Pat. No. 5,936,078 "DNA and Protein for the Diagnosis and Treatment of Alzheimer's Disease."

The vast majority (~95%) of AD cases are late-onset, occurring in the seventh or eighth decade. Late-onset AD is not associated with mutations in APP, PS1 or PS2, yet exhibits neuropathological lesions and symptoms that are similar to those found in early-onset AD. Since late-onset AD is the most common form, it will be referred to herein as AD, while early-onset AD will be referred to as such. The similar neuropathology and outward symptoms of early-onset and late-onset AD have led to the "amyloid cascade hypothesis of AD" (Selkoe, 1994). This model holds that both early and late onset AD result from accumulation of toxic amyloid deposits. The model speculates that in early onset cases, amyloid accumulates rapidly, while in late onset, amyloid accumulates slowly. Much of the research on prevention and treatment of AD has focused on inhibition of amyloid accumulation. However, the amyloid cascade hypothesis remains controversial. Amyloid deposits may be a marker for the disease and not the cause. Translation of Dr. Alzheimer's original work on the neuropathology of AD, relates that he did not favor the view that senile plaques were causative. He states "These changes are found in the basal ganglia, the medulla, the cerebellum and the spinal cord, although there are no plaques at all in those sites or only isolated ones. So we have to conclude that the plaques are not the cause of senile dementia but only an accompanying feature of senile involution of the central nervous system." The italics are his own (Davis and Chisholm, 1999). Many years of research have not resolved this issue (for review of amyloid hypothesis see Selkoe, 1999, for counter argument see Neve et al., 1998). Since the present invention addresses the decreased neuronal metabolism associated with AD, it does not rely on the validity of the amyloid cascade hypothesis.

Several genetic risk factors have been proposed to contribute to the susceptibility to late-onset AD. However, only allelic variation in the lipid transport molecule apolipoprotein E (apoE) has been reproducibly defined as a genetic risk factor for late onset AD. ApoE functions as a ligand in the process of receptor mediated internalization of lipid-rich lipoproteins. These lipoprotein complexes contain phosopholipids, triglycerides, cholesterol and lipoproteins. Several well-characterized allelic variations exist at the apoE locus, and are referred to as apoE2, E3 and E4. ApoE4 is associated with an increased risk of AD, while apoE2 and E3 are not. Increasing the dosage of the E4 allele increases the risk of AD, and lowers the age of onset. However, apoE4 is not an invariant cause of AD. Some individuals, who are homozygous for the E4 allele, do not show AD symptoms even into the ninth decade (Beffert et al., 1998).

A prediction of the observation that apoE4 is associated with AD is that populations with a high prevalence of the E4 allele would also have a high incidence of AD. Yet, the opposite appears to be true. Geographically distinct populations have differing frequencies of apoE alleles. For example, the E4 variant is much more common in Africa versus the UK. In a study of black South Africans and Caucasians from Cambridge, England, the apoE4 allele was present in 48% of Black South Africans compared to 20.8% of Caucasians (Loktionov et al, 1999). In fact, the E4 allele is widespread throughout Africa (Zekraoui et al, 1997). Studies on AD are difficult to do in developing countries, but the studies that have been done show a very low incidence of AD in African communities, 1% versus 6% in US populations (Hall et al, 1998). Even more striking is that the normally robust association between AD and apoE4 is absent in African cases (Osuntokun et al, 1995). This suggests that something is different between native Africans, and US citizens, who are largely of European descent. Perhaps the African populations have some other genetic factor that protects them from AD. This is unlikely, since the incidence of AD in a population of African-Americans from Indianapolis, Ind. USA (6.24%) was found to be much higher than an ethnically similar population in Ibadan, Nigeria (1.4%) (Hall et al, 1998). This suggests that the link between apoE4 and AD has some strong environmental component.

ApoE4 is the ancestral allele, it is most similar to the apoE found in chimpanzees and other primates, while the E2 and E3 alleles arose exclusively in the human lineage, (Hanlon and Rubinsztein, 1995). The changes in apoE were probably brought about by a change in diet in ancestral humans. The E2 and E3 alleles may have arisen in populations as an adaptation to agriculture (Corbo and Scacchi, 1999).

The metabolism of apoE4 in human circulation is different from the non-AD associated apoE3 allele (Gregg et al., 1986). The E4 allele is associated with unusually high levels of circulating lipoproteins (Gregg et al., 1986). In particular, the E4 allele results in decreased rates of VLDL clearance, which leads to higher levels of VLDL and LDL particles in the blood (Knouff, et al. 1999). VLDL and LDL particles contain higher levels of triglycerides than HDL particles. The increased levels of circulating VLDL in individuals carrying apoE4 is due to decreased fatty acid utilization caused by preferential binding of apoE4 to chylomicron and VLDL particles. Prior art has suggested that apoE4 contributes to AD due to inefficient delivery of phospholipids to neurons (for review see Beffert et al., 1998). Yet, apoE4 also clearly contributes to decreased triglyceride usage.

In the central nervous system (CNS), apoE plays a central role in the transportation and redistribution of cholesterol and lipids. The importance of apoE in the brain is highlighted by the absence of other key plasma apolipoproteins such as apoA1 and apoB in the brain (Roheim et al., 1979). ApoE mRNA is found predominantly in astrocytes in the CNS. Astrocytes function as neuronal support cells and can efficiently utilize fatty acids for energy. Since the brain lacks other apolipoproteins, it is uniquely dependent on apoE for lipid transport. While prior art on apoE's role in AD has focused on phospholipid transport, apoE also delivers free fatty acids in the form of triglycerides to astrocytes. Fatty acids delivered by lipoproteins can be converted to ketone bodies by astrocytes for use as an alternative energy source to glucose. An alternative to the neuronal remodeling hypothesis, is that the preferential binding of apoE4 to VLDL particles prevents efficient astrocyte access to triglycerides. Decreased access to triglycerides results in decreased availability of fatty acids and decreased production of ketone bodies, and hence a decreased alternative energy source for cerebral neurons. This reduction in energy supplies may become critical when glucose metabolism in compromised.

Metabolism and Alzheimer's Disease. At the time of this application, the cause of AD remains unknown, yet a large body of evidence has made it clear that Alzheimer's Disease is associated with decreased neuronal metabolism. In 1984, Blass and Zemcov proposed that AD results from a decreased metabolic rate in sub-populations of cholinergic neurons. However, it has become clear that AD is not restricted to cholinergic systems, but involves many types of transmitter systems, and several discrete brain regions. Positron-emission tomography has revealed poor glucose utilization in the brains of AD patients, and this disturbed metabolism can be detected well before clinical signs of dementia occur (Reiman et al., 1996; Messier and Gagnon, 1996; Hoyer, 1998). Additionally, certain populations of cells, such as somatostatin cells of the cortex in AD brain are smaller, and have reduced Golgi apparatus; both indicating decreased metabolic activity (for review see Swaab et al. 1998). Measurements of the cerebral metabolic rates in healthy versus AD patients demonstrated a 20–40% reduction in glucose metabolism in AD patients (Hoyer, 1992). Reduced glucose metabolism results in critically low levels of ATP in AD patients. Also, the severity of decreased metabolism was found to correlate with senile plaque density (Meier-Ruge, et al. 1994).

Additionally, molecular components of insulin signaling and glucose utilization are impaired in AD patients. Glucose is transported across the blood brain barrier and is used as a major fuel source in the adult brain. Consistent with the high level of glucose utilization, the brains of mammals are well supplied with receptors for insulin and IGF, especially in the areas of the cortex and hippocampus, which are important for learning and memory (Frolich et al., 1998). In patients diagnosed with AD, increased densities of insulin receptor were observed in many brain regions, yet the level of tyrosine kinase activity that normally is associated with the insulin receptor was decreased, both relative to age-matched controls (Frolich et al., 1998). The increased density of receptors represents up-regulation of receptor levels to compensate for decreased receptor activity. Activation of the insulin receptor is known to stimulate phosphatidylinositol-3 kinase (PI3K). PI3K activity is reduced in AD patients (Jolles et al., 1992; Zubenko et al., 1999). Furthermore, the density of the major glucose transporters in the brain, GLUTI and GLUT3 were found to be 50% of age matched controls (Simpson and Davies, 1994). The disturbed glucose metabolism in AD has led to the suggestion that AD may be a form of insulin resistance in the brain, similar to type II diabetes (Hoyer, 1998). Inhibition of insulin receptor activity can be exogenously induced in the brains of rats by intracerebroventricular injection of streptozotocin, a known inhibitor of the insulin receptor. These animals develop progressive defects in learning and memory (Lannert and Hoyer, 1998). While glucose utilization is impaired in brains of AD patients, use of the ketone bodies, beta-hydroxybutyrate and acteoacetate is unaffected (Ogawa et al., 1996).

The cause of decreased neuronal metabolism in AD remains unknown. Yet, aging may exacerbate the decreased glucose metabolism in AD. Insulin stimulation of glucose uptake is impaired in the elderly, leading to decreased insulin action and increased insulin resistance (for review see Finch and Cohen, 1997). For example, after a glucose load, mean plasma glucose is 10–30% higher in those over 65 than in younger subjects. Hence, genetic risk factors for AD may result in slightly compromised neuronal metabolism in the brain. These defects would only become apparent later in life when glucose metabolism becomes impaired, and thereby contribute to the development of AD. Since the defects in glucose utilization are limited to the brain in AD, the liver is "unaware" of the state of the brain and does not mobilize fatty acids (see Brain Metabolism section below). Without ketone bodies to use as an energy source, the neurons of the AD patient brain slowly and inexorably starve to death.

Attempts to compensate for reduced cerebral metabolic rates in AD patients has met with some success. Treatment of AD patients with high doses of glucose and insulin increases cognitive scores (Craft et al., 1996). However, since insulin is a polypeptide and must be transported across the blood brain barrier, delivery to the brain is complicated. Therefore, insulin is administered systemically. A large dose of insulin in the blood stream can lead to hyperinsulinemia, which will cause irregularities in other tissues. Both of these shortcomings make this type of therapy difficult and rife with complications. Accordingly, there remains a need for an agent that may increase the cerebral metabolic rate and subsequently the cognitive abilities of a patient suffering from Alzheimer's Disease.

Brain Metabolism. The brain has a very high metabolic rate. For example, it uses 20 percent of the total oxygen consumed in a resting state. Large amounts of ATP are required by neurons of the brain for general cellular functions, maintenance of an electric potential, synthesis of neurotransmitters and synaptic remodeling. Current models propose that under normal physiologic conditions, neurons of the adult human brain depend solely on glucose for energy. Since neurons lack glycogen stores, the brain depends on a continuous supply of glucose from the blood for proper function. Neurons are very specialized and can only efficiently metabolize a few substrates, such as glucose and ketone bodies. This limited metabolic ability makes brain neurons especially vulnerable to changes in energy substrates. Hence, sudden interruption of glucose delivery to the brain results in neuronal damage. Yet, if glucose levels drop gradually, such as during fasting, neurons will begin to metabolize ketone bodies instead of glucose and no neuronal damage will occur.

Neuronal support cells, glial cells, are much more metabolically diverse and can metabolize many substrates, in particular, glial cells are able to utilize fatty acids for cellular respiration. Neurons of the brain cannot efficiently oxidize fatty acids and hence rely on other cells, such as liver cells and astrocytes to oxidize fatty acids and produce ketone bodies. Ketone bodies are produced from the incomplete oxidation of fatty acids and are used to distribute energy throughout the body when glucose levels are low. In a normal Western diet, rich in carbohydrates, insulin levels are high and fatty acids are not utilized for fuel, hence blood ketone body levels are very low, and fat is stored and not used. Current models propose that only during special states, such as neonatal development and periods of starvation, will the brain utilize ketone bodies for fuel. The partial oxidation of fatty acids gives rise to D-beta-hydroxybutyrate (D-3-β-hydroxybutyrate) and acetoacetate, which together with acetone are collectively called ketone bodies. Neonatal mammals are dependent upon milk for development. The major carbon source in milk is fat (carbohydrates make up less then 12% of the caloric content of milk). The fatty acids in milk are oxidized to give rise to ketone bodies, which then diffuse into the blood to provide an energy source for development. Numerous studies have shown that the preferred substrates for respiration in the developing mammalian neonatal brain are ketone bodies. Consistent with this observation is the biochemical finding that astrocytes, oligodendrocytes and neurons all have capacity for efficient ketone body metabolism (for review see Edrmond, 1992). Yet only astrocytes are capable of efficient oxidation of fatty acids to ketone bodies.

The body normally produces small amounts of ketone bodies. However, because they are rapidly utilized, the concentration of ketone bodies in the blood is very low. Blood ketone body concentrations rise on a low carbohydrate diet, during periods of fasting, and in diabetics. In a low carbohydrate diet, blood glucose levels are low, and pancreatic insulin secretion is not stimulated. This triggers the oxidation of fatty acids for use as a fuel source when glucose is limiting. Similarly, during fasting or starvation, liver glycogen stores are quickly depleted, and fat is mobilized in the form of ketone bodies. Since both a low carbohydrate diet and fasting do not result in a rapid drop of blood glucose levels, the body has time to increase blood ketone levels. The rise in blood ketone bodies provides the brain with an alternative fuel source, and no cellular damage occurs. Since the brain has such high energy demands, the liver oxidizes large amounts of fatty acids until the body becomes literally saturated with ketone bodies. Therefore, when an insufficient source of ketone bodies is coupled with poor glucose utilization severe damage to neurons results. Since glial cells are able to utilize a large variety of substrates they are less susceptible to defects in glucose metabolism than are neurons. This is consistent with the observation that glial cells do not degenerate and die in AD (Mattson, 1998).

As discussed in the Metabolism and Alzheimer's Disease section, in AD, neurons of the brain are unable to utilize glucose and begin to starve to death. Since the defects are limited to the brain and peripheral glucose metabolism is normal, the body does not increase production of ketone bodies, therefore neurons of the brain slowly starve to death. Accordingly, there remains a need for an energy source for brain cells that exhibit compromised glucose metabolism. Compromised glucose metabolism is a hallmark of AD; hence administration of such an agent will prove beneficial to those suffering from AD.

Huntington's Disease

Huntington's Disease (HD) is a familial neurodegenerative disorder that afflicts 1/10,000 individuals. It is inherited in an autosomal dominant manner and is characterized by choreiform movements, dementia, and cognitive decline. The disease is produced by genes containing a variably increased (expanded) CAG repeat within the coding region. The size range of the repeats is similar in all diseases; unaffected individuals have fewer than 30 CAG repeats, whereas affected patients usually have more than 40 repeats. The disorder usually has a mid-life onset, between the ages of 30 to 50 years, but may in some cases begin very early or much later in life. The size of the inherited CAG repeat correlates with the severity and age of disease onset. The CAG triplet repeat produces a polyglutamine domain in the expressed proteins. The symptoms are progressive and death typically ensues 10 to 20 years after onset, most often as the result of secondary complications of the movement disorder.

The mutant gene produces huntingtin protein, whose function is unknown. The polyglutamine regions of Huntingtin interact with glyceraldehyde-3-phosphate dehydrogenase (GAPDH), a key glycolytic enzyme. While normal glutamine can bind with GAPDH and cause no harm to the enzyme, binding of mutant Huntingtin inhibits the enzyme. It is believed that the lack of energy being supplied to the brain cells, due to the interference of the Huntingtin protein with GAPDH, in part, causes neuron damage in the basal ganglia and the cerebral cortex. Mitochondrial dysfunction has also been implicated HD.

At least four other diseases are caused by the expanded CAG repeat, and thus also may implicate defective glucose metabolism. These include spinobulbar muscular atrophy, dentatorubral-pallidoluysian atrophy (DRPLA), spino-cerebellar ataxia type 1, and spino-cerebellar ataxia type 3.

Parkinson's Disease

Parkinson's Disease (PD) is widely considered to be the result of degradation of the pre-synaptic dopaminergic neurons in the brain, with a subsequent decrease in the amount of the neurotransmitter dopamine that is being released. Inadequate dopamine release, therefore, leads to the onset of voluntary muscle control disturbances symptomatic of PD.

The motor dysfunction symptoms of PD have been treated in the past using dopamine receptor agonists, monoamine oxidase binding inhibitors, tricyclic antidepressants, anticholinergics, and histamine H1-antagonists. Unfortunately, the main pathologic event, degeneration of the cells in substantia nigra, is not helped by such treatments. The disease continues to progress and, frequently after a certain length of time, dopamine replacement treatment will lose its effectiveness. In addition to motor dysfunction, however, PD is also characterized by neuropsychiatric disorders or symptoms. These include apathy-amotivation, depression, and dementia. PD patients with dementia have been reported to respond less well to standard L-dopa therapy. Moreover, these treatments have little or no benefit with respect to the neuropsychiatric symptoms. Impaired neuronal metabolism is believed to be a contributing factor to PD.

Epilepsy

Epilepsy, sometimes called a seizure disorder, is a chronic medical condition produced by temporary changes in the electrical function of the brain, causing seizures which affect awareness, movement, or sensation. There has been long experience with ketogenic diets, which mimic starvation, in children treated for epilepsy. The diet is a medical therapy and should be used under the careful supervision of a physician and/or dietician. The diet carefully controls caloric input and requires that the child eat only what has been included in the calculations to provide 90% of the day's calories as fats. However, such diets are generally unsuitable for use in adults due to: (1) adverse effects on the circulatory system from incorporation of long chain triglycerides as the primary fat in these diets into cholesterol and the effects of hyperlipidemia; (2) poor patient compliance due to the unappealing nature of the low carbohydrate diet.

Medium Chain Triglycerides (MCT) The metabolism of MCT differs from the more common long chain triglycerides (LCT) due to the physical properties of MCT and their corresponding medium chain fatty acids (MCFA). Due to the short chain length of MCFA, they have lower melting temperatures, for example the melting point of MCFA (C8:0) is 16.7° C., compared with 61.1° C. for the LCFA (C 16:0). Hence, MCT and MCFA are liquid at room temperature. MCT are highly ionized at physiological pH, thus they have much greater solubility in aqueous solutions than LCT. The enhanced solubility and small size of MCT also increases the rate at which fine emulsion particles are formed. These small emulsion particles create increased surface area for action by gastrointestinal lipases. Additionally, medium chain 2-monoglycerides isomerize more rapidly than those of long chain length, allowing for more rapid hydrolysis. Some lipases in the pre-duodenum preferentially hydrolyze MCT to MCFA, which are then partly absorbed directly by stomach mucosa (Hamosh, 1990). Those MCFA which are not absorbed in the stomach, are absorbed directly into the portal vein and not packaged into lipoproteins. LCFA are packaged in chylomicrons and transported via the lymph system, while MCFA are transported via the blood. Since blood transports much more rapidly than lymph, the liver is quickly perfused with MCFA.

In the liver the major metabolic fate of MCFA is oxidation. The fate of LCFA in the liver is dependent on the metabolic state of the organism. LCFA are transported into the mitochondria for oxidation using carnitine palmitoyltransferase I. When conditions favor fat storage, malonyl-CoA is produced as an intermediate in lipogenesis. Malonyl-CoA allosterically inhibits carnitine palmitoyltransferase I, and thereby inhibits LCFA transport into the mitochondria. This feedback mechanism prevents futile cycles of lipolysis and lipogenesis. MCFA are, to large extent, immune to the regulations that control the oxidation of LCFA. MCFA enter the mitochondria largely without the use of carnitine palmitoyltransferase I, therefore MCFA by-pass this regulatory step and are oxidized regardless of the metabolic state of the organism. Importantly, since MCFA enter the liver rapidly and are quickly oxidized, large amounts of ketone bodies are readily produced from MCFA.

Numerous patents relate to use of MCT. None of these patents relate to the specific use of MCT for treatment and prevention of Alzheimer's Disease or other neurodegenerative diseases. Patents such as U.S. Pat. No. 4,528,197 "Controlled triglyceride nutrition for hypercatabolic mammals" and U.S. Pat. No. 4,847,296 "Triglyceride preparations for the prevention of catabolism" relate to the use of MCT to prevent body-wide catabolism that occurs in burns and other serious injuries. Each patent described herein is incorporated by reference herein in its entirety.

SUMMARY OF THE INVENTION

The present invention provides a method of treating or preventing dementia of Alzheimer's type, or other loss of cognitive function caused by reduced neuronal metabolism, comprising administering an effective amount of medium chain triglycerides to a patient in need thereof. Administration may be oral or intravenous. The medium chain triglycerides may be emulsified, and may be coadministered with L-carnitine or a derivative of L-carnitine.

The present invention also provides a method of treating or preventing dementia of Alzheimer's type, or other loss of cognitive function caused by reduced neuronal metabolism, comprising administering an effective amount of free fatty acids derived from medium chain triglycerides to a patient in need thereof.

The present invention also provides a method of treating or preventing dementia of Alzheimer's type, or other loss of cognitive function caused by reduced neuronal metabolism, comprising administering an effective amount of a medium chain triglyceride prodrug to a patient in need thereof.

The present invention also provides a method of treating or preventing dementia of Alzheimer's type, or other loss of cognitive function caused by reduced neuronal metabolism, comprising administering an effective amount of a therapeutic agent which induces utilization of fatty acids and development of ketosis to a patient in need thereof.

The present invention further provides therapeutic agents for the treatment or prevention of dementia of Alzheimer's type, or other loss of cognitive function caused by reduced neuronal metabolism. The present invention also provides pharmaceutical compositions. In one instance the pharmaceutical composition comprises a medium chain triglyceride and a sugar, including monosaccharides, disaccharides, polysaccharides, and mixtures thereof.

The present invention also provides a pharmaceutical composition comprising a medium chain triglyceride and a TCA cycle intermediate or a metabolic precursor of a TCA intermediate.

The present invention also provides a pharmaceutical composition comprising a medium chain triglyceride and a ketone body or metabolic precursor of a ketone body, including β-hydroxybutytate, acteoacetate, metabolic precursors of β-hydroxybutyrate or acteoacetate, a physiologically acceptable salt or ester of a polymer or oligomers, and mixtures thereof. The present invention also provides a pharmaceutical composition comprising a medium chain triglyceride and a metabolic adjuvant, such as a vitamin, a mineral, an antioxidant, an energy-enhancing compound, and mixtures thereof, Coenzyme CoQ-10, creatine, L-carnitine, n-acetyl-carnitine, L-camitine derivatives, and mixtures thereof.

The present invention also provides therapeutic agents which are derivatives of MCT, and can include ketone body precursors and essential fatty acids esterified to a the glycerol backbone.

The present invention further provides pharmaceutical compositions comprising a medium chain triglyceride and a therapeutic agent selected from the group consisting of acetylcholinesterase inhibitors, acetylcholine synthesis modulators, acetylcholine storage modulators, acetylcholine release modulators, anti-inflammatory agents, estrogen or estrogen derivatives, insulin sensitizing agents, β-amyloid plaque removal agents (including vaccines), inhibitors of β-amyloid plaque formation, γ-secretase modulators, pyruvate dehydrogenase complex modulators, α-ketoglutarate dehydrogenase complex modulators, neurotrophic growth factors (e.g., BDNF), ceramides or ceramide analogs, and/or NMDA glutamate receptor antagonists.

The present invention further provides a pharmaceutical composition comprising a medium-chain triglyceride and at least one therapeutic agent which induces utilization of fatty acids, including a PPAR-garnma agonist such as aspirin, ibuprofen, ketoprofen, and naproxen, and thiazolidinedione drugs, a statin drug such as Liptor or Zocor, fibrate drugs such as Bezafibrate, ciprofibrate, fenofibrate or Gemfibrozil, caffeine, and ephedra.

The present inventin also provides a method of individualizing a treatment for Alzheimer's Disease, comprising determining a patient's apolipoprotein E genotype and providing a pharmaceutical composition comprising medium chain triglycerides which provides an ketone body level effective for treatment of Alzheimer's Disease for said genotype to individualize the treatment for Alzheimer's Disease.

The present invention further provides a method of elevating ketone body levels comprising administering a medium chain triglyceride to a patient in need thereof, The present invention also provides methods of increasing cognitive ability in a patient suffering from Alzheimer's Disease, comprising administering medium chain triglycerides to a patient in need thereof or comprising increasing ketone body levels in the patient.

The present invention also provides a method of treating reduced neuronal metabolism comprising administering a therapeutic agent which induces utilization of fatty acids, including a PPAR-gamma agonist, a statin drug, and a fibrate drug.

The present invention provides a method of treating or preventing dementia of Alzheimer's type, or other loss of cognitive function caused by reduced neuronal metabolism, comprising administering an agent capable of increasing blood serum ketone body levels to a patient in need thereof.

The present invention provides a pharmaceutical composition comprising β-hydroxybutyrate, acteoacetate, metabolic precursors of β-hydroxybutyrate or acteoacetate, mixtures of the foregoing, and one selected from the group consisting of a PPAR-gamma agonist, a statin drug, and a fibrate drug.

The present invention also provides a method of treating or preventing dementia of Alzheimer's type, or other loss of cognitive function caused by reduced neuronal metabolism, comprising administering an effective amount of a pharmaceutical composition of claim 51 to a patient in need thereof.

DETAILED DESCRIPTION OF THE INVENTION

It is the novel insight of this invention that medium chain triglycerides (MCT) and their associated fatty acids are useful as a treatment and preventative measure for AD patients. As used herein, "patient" refers to any mammal, including humans, that may benefit from treatment of disease and conditions resulting from reduced neuronal metabolism. As used herein, reduced neuronal metabolism refers to all possible mechanisms that could lead to a reduction in neuronal metabolism. Such mechanisms include, but are not limited to mitochondrial dysfunction, free radical attack, defective glucose transport or glycolysis, imbalance in membrane ionic potential, dysfunction in calcium flux, and the like. MCT are composed of fatty acids with chain lengths of between 5–12 carbons. A diet rich in MCT results in high blood ketone levels. High blood ketone levels will provide an energy source for brain cells that have compromised glucose metabolism via the rapid oxidation of MCFA to ketone bodies.

The background of this invention supports the present invention in the following ways.

(1) Neurons of the brain can use both glucose and ketone bodies for respiration. (2) The neurons of Alzheimer's Disease patients have well documented defects in glucose metabolism. (3) Known genetic risk factors for Alzheimer's Disease are associated with lipid and cholesterol transport, suggesting defects in triglyceride usage that may underlie susceptibility to Alzheimer's Disease. (4) ingestion of MCT will lead to increased levels of blood ketone bodies and thereby provide energy to starving brain neurons. Hence, supplementation of Alzheimer's Disease patients with MCT will restore neuronal metabolism. Additionally, defects in neuronal metabolism in Huntington's Disease, Parkinson's Disease, and epilepsy and other related neurodegenerative diseases such as Wernicke-Korsakoff Disease and possibly schizophrenia will be benefited by high blood ketone levels, derived from MCT that provide an energy source for brain cells. As used herein, "high blood ketone levels" refers to levels of at least about 0.1 mM. More preferably, high blood ketone levels refers to levels in the range of 0.1 to 50 mM, more preferably in the range of 0.2–20 mM, more preferably in the range of 0.3–5 mM, and more preferably in the range of 0.5–2 mM.

It is also the novel insight of this invention that a combination of MCTs and therapeutic agents that increase the utilization of fatty acids by any mechanism are useful as a treatment and preventative measure for AD patients.

The present invention provides a method of treating or preventing dementia of Alzheimer's type, or other loss of cognitive function caused by reduced neuronal metabolism, comprising administering an effective amount of medium chain triglycerides to a patient in need thereof. Generally, an effective amount is an amount effective to either (1) reduce the symptoms of the disease sought to be treated or (2) induce a pharmacological change relevant to treating the disease sought to be treated. For Alzheimer's Disease, an effective amount includes an amount effective to: increase cognitive scores; slow the progression of dementia; or increase the life expectancy of the affected patient. As used herein, medium chain triglycerides of this invention are represented by the following formula:

wherein $R_1$ is independently selected from the group consisting of a fatty acid residue esterified to a glycerol backbone having 5–12 carbons in the carbon backbone ($C_5$ to $C_{12}$ fatty acids), a saturated fatty acid residue esterified to a glycerol backbone having 5–12 carbons in the carbon backbone ($C_5$ to $C_{12}$ fatty acids), an unsaturated fatty acid residue esterified to a glycerol backbone having 5–12 carbons in the carbon backbone ($C_5$ to $C_{12}$ fatty acids), and derivatives of any of the foregoing. The structured lipids of this invention may be prepared by any process known in the art, such as direct esterification, rearrangement, fractionation, transesterification, or the like. For example the lipids may be prepared by the rearrangement of a vegetable oil such as coconut oil.

In a preferred embodiment, the method comprises the use of MCTs wherein $R_1$ is a fatty acid containing a six-carbon backbone (tri-C6:0). Tri-C6:0 MCT are absorbed very rapidly by the gastrointestinal track in a number of animal model systems (Odle 1997). The high rate of absorption results in rapid perfusion of the liver, and a potent ketogenic response. In another preferred embodiment, the method comprises the use of MCTs wherein $R_1$ is a fatty acid containing a eight-carbon backbone (tri-C8:0). Additionally, utilization of tri-C6.0 MCT and tri-C8:0 MCT can be increased by emulsification. Emulsification of lipids increases the surface area for action by lipases, resulting in more rapid hydrolysis. Methods for emulsification of these triglycerides are well known to those skilled in the art.

In Example 3, the inventor demonstrates the efficacy of tri-C8:0 medium chain triglycerides (MCT) in the treatment of AD. In this example the inventor reveals several key aspects of the invention. First, MCT induce elevated ketone body levels in the elderly (mean age =74.7 years). Second, MCT induce different ketone body levels in different subjects based on their apolipoprotein E genotype. Third, MCT treatments result in improved performance on established Alzheimer Disease cognitive measures (ADAS-cog). Fourth, improved performance on ADAS-cog test was influenced by the subject's apolipoprotein E genotype. Fifth, higher ketone body levels were associated with greater improvement in a second measure of cognitive performance (the paragraph recall test) with MCT treatment.

In another preferred embodiment, the invention provides a method of treating or preventing dementia of Alzheimer's type, or other loss of cognitive function caused by reduced neuronal metabolism, comprising administering an effective amount of free fatty acids, which may be derived from medium chain triglycerides, to a patient in need thereof. Because MCT are metabolized to produce medium chain fatty acids, which are oxidized, the administration of free fatty acids and/or ketone bodies have the same effect as the administration of MCT themselves.

In another preferred embodiment, the invention comprises the coadministration of emulsified tri-C6:0 MCT and L-carnitine or a derivative of L-carnitine. Slight increases in MCFA oxidation have been noted when MCT are combined with L-carnitine (Odle, 1997). Thus in the present invention emulsified MCT are combined with L-carnitine at doses required to increase the utilization of said MCT. The dosage of L-carnitine and MCT will vary according to the condition of the host, method of delivery, and other factors known to those skilled in the art, and will be of sufficient quantity to raise blood ketone levels to a degree required to treat and prevent Alzbeimer's Disease. Derivatives of L-carnitine which may be used in the present invention include but are not limited to decanoylcarnitine, hexanoylcarnitine, caproylcarnitine, lauroylcarnitine, octanoylcarnitine, stearoylcarnitine, myristoylcarnitine, acetyl-L-carnitine, O-Acetyl-L-carnitine, and palmitoyl-L-carnitine.

Therapeutically effective amounts of the therapeutic agents can be any amount or dose sufficient to bring about the desired anti-dementia effect and depend, in part, on the severity and stage of the condition, the size and condition of the patient, as well as other factors readily known to those skilled in the art. The dosages can be given as a single dose, or as several doses, for example, divided over the course of several weeks.

In one embodiment, the MCT or fatty acids are administered orally. In another embodiment, the MCT are administered intravenously. Oral administration of MCT and preparations of intravenous MCT solutions are well known to those skilled in the art.

Oral and intravenous administration of MCT or fatty acids result in hyperketonemia. Hyperketonemia results in ketone bodies being utilized for energy in the brain even in the presence of glucose. Additionally, hyperketonemia results in a substantial (39%) increase in cerebral blood flow (Hasselbalch et al. 1996). Hyperketonemia has been reported to reduce cognitive dysfunction associated with systemic hypoglycemia in normal humans (Veneman et al. 1994). Please note that systemic hypoglycemia is distinct from the local defects in glucose metabolism that occur in AD.

In another embodiment, the invention provides the subject compounds in the form of one or more prodrugs, which can be metabolically converted to the subject compounds by the recipient host. As used herein, a prodrug is a compound that exhibits pharmacological activity after undergoing a chemical transformation in the body. The said prodrugs will be administered in a dosage required to increase blood ketone bodies to a level required to treat and prevent the occurrence of Alzheimer's Disease. A wide variety of prodrug formulations are known in the art. For example, prodrug bonds may be hydrolyzable, such as esters or anhydrides, or enzymatically biodegradable, such as amides.

This invention also provides a therapeutic agent for the treatment or prevention of dementia of Alzheimer's type, or other loss of cognitive function caused by reduced neuronal metabolism, comprising medium chain triglycerides. In a preferred embodiment, the therapeutic agent is provided in administratively convenient formulations of the compositions including dosage units incorporated into a variety of containers. Dosages of the MCT are preferably administered in an effective amount, in order to produce ketone body concentrations sufficient to increase the cognitive ability of patients afflicted with AD or other states of reduced neuronal metabolism. For example, for the ketone body, D-beta-hydroxybutyrate, blood levels are raised to about 0.1–50 mM 0.1–50 (measured by urinary excretion in the range of about 5 mg/dL to about 160 mg/dL), more preferably raised to about 0.2–20 mM, more preferably raised to about 0.3–5 mM, more preferably raised to about 0.5–2 mM, although variations will necessarily occur depending on the formulation and host, for example. Effective amount dosages of other MCT will be apparent to those skilled in the art. In one embodiment, an MCT dose will be in the range of 0.05 g/kg day to 10 g/kg/day of MCT. More preferably, the dose will be in the range of 0.25 g/kg day to 5 g/kg/day of MCT. More preferably, the dose will be in the range of 0.5 g/kg/day to 2 g/kg day of MCT. Convenient unit dosage containers and/or formulations include tablets, capsules, lozenges, troches, hard candies, nutritional bars, nutritional drinks, metered sprays, creams, and suppositories, among others. The compositions may be combined with a pharmaceutically acceptable excipient such as gelatin, an oil, and/or other pharmaceutically active agent(s). For example, the compositions may be advantageously combined and/or used in combination with other therapeutic or prophylactic agents, different from the subject compounds.

In many instances, administration in conjunction with the subject compositions enhances the efficacy of such agents. For example, the compounds may be advantageously used in conjunction with antioxidants, compounds that enhance the efficiency of glucose utilization, and mixtures thereof, (see e.g. Goodman et al. 1996).

In a preferred embodiment the human subject is intravenously infused with MCT, MCFA (medium chain fatty acids) and/or ketone bodies directly, to a level required to treat and prevent the occurrence of Alzheimer's Disease. Preparation of intravenous lipid, and ketone body solutions is well known to those skilled in the art.

In a preferred embodiment, the invention provides a formulation comprising a mixture of MCT and carnitine to provide elevated blood ketone levels. The nature of such formulations will depend on the duration and route of administration. Such formulations will be in the range of 0.05 g/kg/day to 10 g/kg/day of MCT and 0.05 mg/kg/day to 10 mg/kg/day of carnitine or its derivatives. In one embodiment, an MCT dose will be in the range of 0.05 g/kg/day to 10 g/kg/day of MCT. More preferably, the dose will be in the range of 0.25 g/kg/day to 5 g/kg/day of MCT. More preferably, the dose will be in the range of 0.5 g/kg/day to 2 g/kg/day of MCT. In some embodiments, a carnitine or carnitine derivative dose will be in the range of 0.05 g/kg/day to 10 g/kg/day. More preferably, the carnitine or carnitine derivative dose will be in the range of 0.1 g/kg/day to 5 g/kg/day. More preferably, the carnitine or carnitine derivative dose will be in the range of 0.5 g/kg/day to 1 g/kg/day. Variations will necessarily occur depending on the formulation and/or host, for example.

A particularly preferred formulation comprises a range of 1–500 g of emulsified MCT combined with 1–2000 mg of carnitine. An even more preferred formulation comprises 50 g MCT (95% triC8:0) emulsified with 50 g of mono- and di-glycerides combined with 500 mg of L-carnitine. Such a formulation is well tolerated and induces hyperketonemia for 3–4 hours in healthy human subjects.

In another embodiment, the invention provides the recipient with a therapeutic agent which enhances endogenous fatty acid metabolism by the recipient. The said therapeutic agent will be administered in a dosage required to increase blood ketone bodies to a level required to treat and prevent the occurrence of Alzheimer's Disease. Ketone bodies are produced continuously by oxidation of fatty acids in tissues that are capable of such oxidation. The major organ for fatty acid oxidation is the liver. Under normal physiological conditions ketone bodies are rapidly utilized and cleared from the blood. Under some conditions, such as starvation or low carbohydrate diet, ketone bodies are produced in excess and accumulate in the blood stream. Compounds that mimic the effect of increasing oxidation of fatty acids will raise ketone body concentration to a level to provide an alternative energy source for neuronal cells with compromised metabolism. Since the efficacy of such compounds derives from their ability to increase fatty acid utilization and raise blood ketone body concentration they are dependent on the embodiments of the present invention.

Compounds that mimic the effect of increasing oxidation of fatty acids and will raise ketone body concentration include but are not limited to the ketone bodies, D-β-hydroxybutyrate and aceotoacetate, and metabolic precursors of these. The term metabolic precursor, as used herein, refers to compounds that comprise 1,3 butane diol, acetoacetyl or D-β-hydroxybutyrate moieties such as acetoacetyl-1-1,3-butane diol, acetoacetyl-D-β-hydroxybutyate, and acetoacetylglycerol. Esters of any such compounds with monohydric, dihydric or trihydric alcohols is also envisaged. Metabolic precursors also include polyesters of D-β-hydroxybutyrate, and acetoaoacetate esters of D-β-hydroxybutyrate. Polyesters of D-β-hydroxybutyrate include oligomers of this polymer designed to be readily digestible and/or metabolized by humans or animals. These preferably are of 2 to 100 repeats long, typically 2 to 20 repeats long, and most conveniently from 3 to 10 repeats long. Examples of poly D->hydroxybutyrate or terminally oxidized poly-D-β-hydroxybutyrate esters useable as ketone body precursors are given below:

compound 1 compound 2 compound 3

In each case n is selected such that the polymer or oligomer is readily metabolized on administration to a human or animal body to provide elevated ketone body levels in blood. Preferred values of n are integers of 0 to 1,000, more preferably 0 to 200, still more preferably 1 to 50, most preferably 1 to 20, particularly conveniently being from 3 to 5. In each case m is an integer of 1 or more, a complex thereof with one or more cations or a salt thereof for use in therapy or nutrition. Examples of cations and typical physiological salts are described herein, and additionally include sodium, potassium, magnesium, calcium, each balanced by a physiological counter-ion forming a salt complex, L-lysine, L-arginine, methyl glucamine, and others known to those skilled in the art. The preparation and use of such metabolic precursors is detailed in Veech, WO 98/41201, and Veech, WO 00/15216, each of which is incorporated by reference herein in its entirety.

The present invention provides a compound of the formula:

wherein $R_2$ is independently selected from the group consisting of $R_1$, an essential fatty acid esterified to a glycerol backbone, β-hydroxybutyrate esterified to a glycerol backbone, acetoacetate esterified to the glycerol backbone, compound 1 esterified to a glycerol backbone, compound 2 esterified to a glycerol backbone, and compound 3 esterified to a glycerol backbone, with the proviso that at least one of $R_2$ is $R_1$. This compound will provide increased levels of ketone bodies due to the MCT character of the molecule where $R_2$ is a ketone body precursor of the molecule. Additionally, where $R_2$ is an essential fatty acid, namely, linoleic or arachidonic acids, the compound has the additional advantage of providing the essential fatty acid.

Accordingly, the present invention also provides a method of treating or preventing dementia of Alzheimer's type, or other loss of cognitive function caused by reduced neuronal metabolism, comprising administering an effective amount of the foregoing compound to a patient in need thereof.

In another embodiment, the invention provides a therapeutic compound or mixture of compounds, the composition and dosage of which is influenced by the patients' genotype, in particular the alleles of apoliproprotein E gene. In Example 3 the inventor discloses that non-E4 carriers performed better than those with the E4 allele when elevated ketone body levels were induced with MCT. Also, those with the E4 allele had higher fasting ketone body levels and the levels continued to rise at the two hour time interval. Therefore, E4 carriers may require higher ketone levels or agents that increase the ability to use the ketone bodies that are present. Accordingly, a preferred embodiment consists of a dose of MCT combined with agents that increase the utilization of fats, MCT or ketone bodies. Examples of agents that increase utilization of fatty acids may be selected from a group comprising of, but not limited to, non-steroidal anti-inflammatory agents (NSAIDs), statin drugs (such as Lipitor® and Zocor®) and fibrates. Examples of NSAIDs include: aspirin, ibuprofen (Advil, Nuprin, and others), ketoprofen (Orudis KT, Actron), and naproxen (Aleve).

NSAIDs function, in part, as PPAR-gamma agonists. Increasing PPAR-gamma activity increases the expression of genes associated with fatty acid metabolism such as FATP (for review see (Gelman, Fruchart et al. 1999)). Accordingly, a combination of MCT and PPAR-gamma agonists will prove beneficial to individuals with decreased neuronal metabolism. In a preferred embodiment the PPAR-gamma agonist is an NSAID.

Statins are a class of drugs with pleiotropic effects, the best characterized being inhibition of the enzyme 3-hydroxy-3-methylglutaryl CoA reductase, a key rate step in cholesterol synthesis. Statins also have other physiologic affects such as vasodilatory, anti-thrombotic, antioxidant, anti-proliferative, anti-inflammatory and plaque stabilizing properties. Additionally, statins cause a reduction in circulating triglyceride rich lipoproteins by increasing the levels of lipoprotein lipase while also decreasing apolipoprotein C-III (an inhibitor of lipoprotein lipase) (Schoonjans, Peinado-Onsurbe et al. 1999). Accordingly, administration of statins results in increased fatty acid usage, which can act synergistically with MCT administration. This should prove especially beneficial to ApoE4 carriers. One embodiment of this invention would be combination therapy consisting of statins and MCT.

Fibrates, such as Bezafibrate, ciprofibrate, fenofibrate and Gemfibrozil, are a class of lipid lowering drugs. They act as PPAR-alpha agonists and similar to statins they increase lipoprotein lipase, apoaI and apoAI transcription and reduce levels of apoCIII (Staels, Dallongeville et al. 1998). As such they have a major impact on levels of triglyceride rich lipoproteins in the plasma, presumably by increasing the use of fatty acids by peripheral tissues. Accordingly, the present invention discloses that fibrates alone or in combination with MCT would prove beneficial to patients with reduced neuronal metabolism such as those with Alzheimer's Disease.

Caffeine and ephedra alkaloids are commonly used in over the counter dietary supplements. Ephedra alkaloids are commonly derived from plant sources such as ma-huang (Ephedra sinica). The combination of caffeine and ephedra stimulate the use of fat. Ephedra alkaloids are similar in structure to adrenaline and activate beta-adenergic receptors on cell surfaces. These adenergic receptors signal through cyclic AMP (cAMP) to increase the use of fatty acids cAMP is normally degraded by phosphodiesterase activity. One of the functions of caffeine is to inhibit phosphodiesterase activity and thereby increase cAMP mediated signaling. Therefore caffeine potentiates the activity of the ephedra alkaloids. Accordingly, the present invention discloses that ephedra alkaloids alone can provide a treatment or prevention for conditions of reduced neuronal metabolism. Additionally, it is disclosed that ephedra alkaloids in combination with caffeine can provide a treatment or prevention for conditions of reduced neuronal metabolism. Accordingly, it is disclosed that a combination of MCT with ephedra, or MCT with caffeine, or MCT, ephedra alkaloids and caffeine together can provide a treatment or prevention for conditions of reduced neuronal metabolism.

Figure 1:
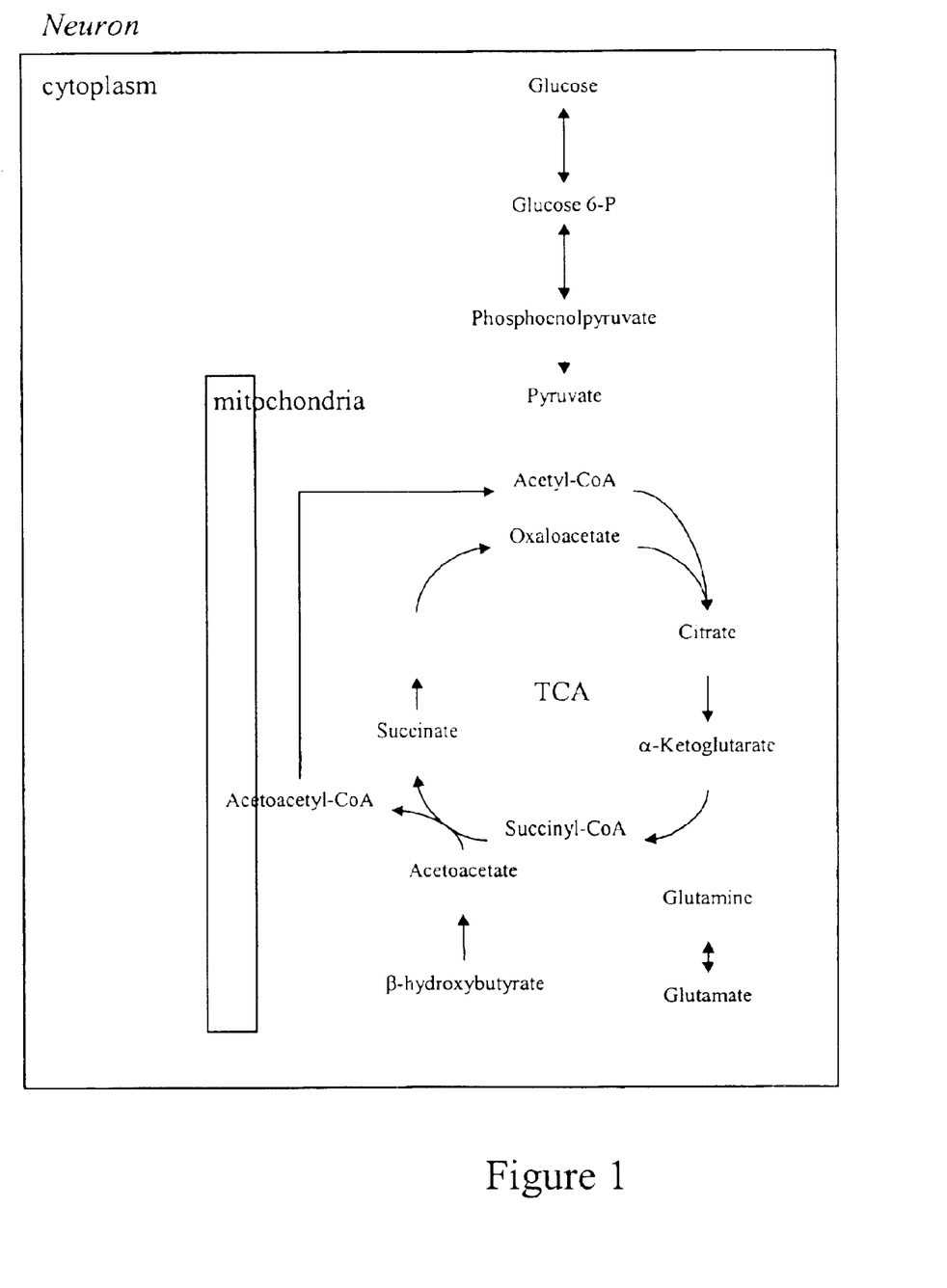
FIG. 1 shows a schematic of the TCA cycle as it occurs in the cell.

Ketone bodies are used by neurons as a source of Acetyl-CoA. Acetyl-CoA is combined with oxaloacetate to form citrate in the Krebs' cycle, or citric acid cycle (TCA cycle) (see FIG. 1). It is important for neurons to have a source of Acetyl-CoA as well as TCA cycle intermediates to maintain efficient energy metabolism. Yet, neurons lose TCA cycle intermediates to synthesis reactions, such as the formation of glutamate. Neurons also lack pyruvate carboxylase and malic enzyme so they cannot replenish TCA cycle intermediates from pyruvate (Hertz, Yu et al. 2000). Accordingly, the present invention discloses that a combination 110 of ketone bodies with a source of TCA cycle intermediates will be beneficial to conditions of reduced neuronal metabolism. TCA cycle intermediates are selected from a group consisting of citric acid, aconitic acid, isocitric acid, α-ketoglutaric acid, succinic acid, fumaric acid, malic acid, oxaloacetic acid, and mixtures thereof. One embodiment of the invention is a combination of TCA cycle intermediates with MCT in a formulation to increase efficiency of the TCA.

Another source of TCA cycle intermediates are compounds that are converted to TCA cycle intermediates within the body (TCA intermediate precursors). Examples of such compounds are 2-ketoAhydroxypropanol, 2,4-dihydroxybutanol, 2-keto-4-hydroxybutanol, 2,4-dihydroxybutyric acid, 2-keto4-hydroxybutyric acid, aspartates as well as mono- and di-alkyl oxaloacetates, pyruvate and glucose-6-phosphate. Accordingly, the present invention discloses that a combination of TCA intermediate precursors with ketone bodies will be beneficial for the treatment and prevention of diseases resulting from reduced metabolism. Also, the present invention discloses that MCT combined with TCA intermediate precursors will be beneficial for the treatment and prevention of diseases resulting from reduced metabolism.

The present invention further discloses that additional sources of TCA cycle intermediates and Acetyl-CoA can be advantageously combined with ketone body therapy. Sources of TCA cycle intermediates and Acetyl-CoA include mono- and di-saccharides as well as triglycerides of various chain lengths and structures.

Further benefit can be derived from formulation of a pharmaceutical composition that includes metabolic adjuvants. Metabolic adjuvants include vitamins, minerals, antioxidants and other related compounds. Such compounds may be chosen from a list that includes but is not limited to; ascorbic acid, biotin, calcitriol, cobalamin, folic acid, niacin, pantothenic acid, pyridoxine, retinol, retinal (retinaldehyde), retinoic acid, riboflavin, thiamin, a-tocopherol, phytylmenaquinone, multiprenylmenaquinone, calcium, magnesium, sodium, aluminum, zinc, potassium, chromium, vanadium, selenium, phosphorous, manganese, iron, fluorine, copper, cobalt, molybdenum, iodine. Accordingly a combination of ingredients chosen from: metabolic adjuvants, compounds that increase ketone body levels, and TCA cycle intermediates, will prove beneficial for treatment and prevention of diseases associated with decreased metabolism, including Alzheimer's Disease, Parkinson's Disease, Huntington's Disease, and epilepsy.

With regard to epilepsy, the prior art provides descriptions of ketogenic diets in which fat is high and carbohydrates are limited. In summary, the rationale of such diets is that intake of high amounts of fat, whether long-chain or medium-chain triglycerides, can increase blood ketone levels in the context of a highly-regimented diet in which carbohydrate levels are absent or limited. Limitation of carbohydrate and insulin are believed to prevent re-esterification in adipose tissue. In contrast to the prior art, the present invention provides for and claims the administration of medium chain triglycerides outside of the context of the ketogenic diet.

Furthermore, the EXAMPLES section below provides exemplary formulations which include carbohydrates.

Although the ketogenic diet has been known for decades, there does not appear to be any prior art teaching or suggesting that MCT therapy be used to treat Alzheimer's Disease or other cognitive disorders.

Additional metabolic adjuvants include energy enhancing compounds, such as Coenzyme CoQ-10, creatine, L-carnitine, n-acetyl-carnitine, L-carnitine derivatives, and mixtures thereof.

These compounds enhance energy production by a variety of means. Carnitine will increase the metabolism of fatty acids. CoQ-10 serves as an electron carrier during electron transport within the mitochondria Accordingly, addition of such compounds with MCT will increase metabolic efficiency especially in individuals who may be nutritionally deprived.

Administration of MCT, and especially triglycerides composed of C6 and C8 fatty acid residues, result in elevated ketone body levels even if large amounts of carbohydrate are consumed at the same time (for overview see (Odle 1997); see also copending United States Patent Provisional Patent Application Ser. No. 60/323,995, "Drug Targets for Alzheimer's Disease and Other Diseases Associated with Decreased Neuronal Metabolism," filed Sep. 21, 2001). The advantages of the Applicant's approach are clear, since careful monitoring of what is eaten is not required and compliance is much simpler. Further benefit can be derived from formulation of a pharmaceutical composition comprising MCT and other therapeutic agents which are used in the treatment of Alzheimer's Disease, Parkinson's Disease, Huntington's Disease, or epilepsy. Such therapeutic agents include acetylcholinesterase inhibitors, acetylcholine synthesis modulators, acetylcholine storage modulators, acetylcholine release modulators, anti-inflammatory agents, estrogen or estrogen derivatives, insulin sensitizing agents, P-amyloid plaque removal agents (including vaccines), inhibitors of 0-amyloid plaque formation, γ-secretase modulators, pyruvate dehydrogenase complex modulators, neurotrophic growth factors (e.g., BDNF), ceramides or ceramide analogs, and/or NMDA glutamate receptor antagonists for overview of such treatments see (Selkoe 2001; Bullock 2002)). While such treatments are still in the experimental stage it is the novel insight of the present invention that said treatments be advantageously combined with increased fatty acid/ketone body usage as described herein.

Advantages

From the description above, a number of advantages of the invention for treating and preventing Alzheimer's Disease become evident:

(a) Prior art on AD has largely focused on prevention and clearance of amyloid deposits.

The role of these amyloid deposits in AD remains controversial and may only be a marker for some other pathology. The present invention provides a novel route for treatment and prevention of AD based on alleviating the reduced neuronal metabolism associated with AD, and not with aspects of amyloid accumulation.

(b) Current treatments for AD are merely palliative and do not address the reduced neuronal metabolism associated with AD. Ingestion of medium chain triglycerides as a nutritional supplement is a simple method to provide neuronal cells, in which glucose metabolism is compromised, with ketone bodies as a metabolic substrate.

(c) Increased blood levels of ketone bodies can be achieved by a diet rich in medium chain triglycerides.

(d) Medium chain triglycerides can be infused intravenously into patients or administered orally.

(e) Levels of ketone bodies can be easily measured in urine or blood by commercially available products (e.g., Ketostix®, Bayer, Inc.).

Accordingly, the reader will see that the use of medium chain triglycerides (MCT) or fatty acids as a treatment and preventative measure of Alzheimer's Disease (AD) provides a novel means of alleviating reduced neuronal metabolism associated with AD. It is the novel and significant insight of the present invention that use of MCT results in hyperketonemia which will provide increased neuronal metabolism for diseases associated with reduced neuronal metabolism, such as AD, ALS, Parkinson's Disease and Huntington's Disease. Although the description above contains many specificities, these should not be construed as limiting the scope of the invention but merely as providing illustrations for some of the presently preferred embodiments of this invention. For example, supplementation with MCT may prove more effective when combined with insulin sensitizing agents such as vanadyl sulfate, chromium picolinate, and vitamin E. Such agents may function to increase glucose utilization in compromised neurons and work synergistically with hyperketonemia. In another example MCT can be combined with compounds that increase the rates of fatty acid utilization such as L-carnitine and its derivatives. Mixtures of such compounds may synergistically increase levels of circulating ketone bodies.

Thus the scope of the invention should be determined by the appended claims and their legal equivalents, rather than by the examples given.

REFERENCES

Throughout the specification, citations to a number of references have been made. Each of these references is incorporated by reference herein in its entirety. Many of the references are summarized here:

Beffert, U., Danik, M., Krzywkowski, P., Ramassamy, C., Berrada, F., and Poirier, J. (1998) The neurobiology of apolipoproteins and their receptors in the CNS and Alzheimer's disease. Brain Res Brain Res Rev 27:119–42.

Blass, J. P., and Zemcov, A. (1984) Alzheimer's disease. A metabolic systems degeneration? Neurochem Pathol 2:103–14.

Craft, S., Newcomer, J., Kanne, S., Dagogo-Jack, S., Cryer, P., Sheline, Y., Luby, J., Dagogo-Jack, A., and Alderson, A. (1996) Memory improvement following induced hyperinsulinemia in Alzheimer's disease. Neurobiol Aging 17:123–30.

Corbo, R. M. and Sacchi, R. (1999) Apoliporpotein E (APOE) allele distribution in the world. Is APOE*4 a 'thrifty' allele. Ann Hum Genet 63:301–10.

Davis, J. N., and Chisholm, J. C. (1999). Alois Alzheimer and the amyloid debate. Nature 400:810.

Edmond, J. (1992) Energy metabolism in developing brain cells. Can J Physiol Pharmacol 70:S118–29.

Evans, D. A., Funkenstein, H. H., Albert, M. S., Scherr, P. A., Cook, N. R., Chown, M. J., Hebert, L. E., Hennekens, C. H., and Taylor, J. O. (1989) Prevalence of Alzheimer's disease in a community population of older persons. Higher than previously reported. JAMA 262:2551–6.

Finch, C. E., and Cohen, D. M. (1997) Aging, metabolism, and Alzheimer disease: review and hypotheses. Exp Neuro! 143:82–102.

Frolich, L., Blum-Degen, D., Bernstein, H. G., Engeisberger, S., Humnich, J., Laufer, S., Muschner, D., Thalheimer, A., Turk, A., Hoyer, S., Zochling, R., Boissl, K. W., Jellinger, K., and Riederer, P. (1998) Brain insulin and insulin receptors in aging and sporadic Alzheimer's disease. JNeural Transm 105:423–38.

Bullock, R. (2002). "New drugs for Alzheimer's disease and other dementias." *Br J Psychiatrv* 180: 135–9.

Gelman, L., J. C. Fruchart, et al. (1999). "An update on the mechanisms of action of the peroxisome proliferator-activated receptors (PPARs) and their roles in inflammation and cancer." *Cell Mol Life Sci* 55(6–7): 932–43.

Hertz, L., A. C. Yu, et al. (2000). "Neuronal-astrocytic and cytosolic-mitochondrial metabolite trafficking during brain activation, hyperammonemia and energy deprivation." *Neurochem Int* 37(2–3): 83–102.

Schoonjans, K., J. Peinado-Onsurbe, et al. (1999). "3-Hydroxy-3-methylglutaryl CoA reductase inhibitors reduce serum triglyceride levels through modulation of apolipoprotein C-III and lipoprotein lipase." *FEBS Lett* 452(3):1604.

Selkoe, D. J. (2001). "Alzheimer's disease: genes, proteins, and therapy." *Physiol Rev* 81(2): 741–66.

Staels, B., J. Dallongeville, et al. (1998). "Mechanism of action of fibrates on lipid and lipoprotein metabolism." *Circulation* 98(19):2088–93.

Gregg, R. E., Zech, L. A., Schaefer, E. J., Stark, D., Wilson, D., and Brewer, H. B. Jr. (1986). Abnormal in vivo metabolism of apolipoprotein E4 in humans. J Clin Invest 78:815–21.

Goodman, L. S., Limbird, L. E., Mitinoff, P. B., Gilman, A. G., and Hardman, J. G. (editors). (1996). The Pharmacological Basis of Therapeutics, 9.sup.th Ed., McGraw-Hill.

Hall K., Gureje O., Gao S., Ogunriyi A., Hui S. L., Baiyewu O., Unverzagt F. W., Oluwole S., Hendrie H. C. (1998) Risk factors and Alzheimer's disease: a comparative study of two communities. Aust N Z J Psychiatry 32:698–706.

Hamosh, M. (1990) In: Lingual and Gastric Lipases: Their role in fat digestion. CRC press, Boca Raton, Fla.

Hanlon C. S., and Rubinsztein D. C. (1995) Arginine residues at codons 112 and 158 in the apolipoprotein E gene correspond to the ancestral state in humans. Atherosclerosis 112:85–90.

Hasselbalch, S. G., Madsen, P. L., Hageman, L. P., Olsen, K. S., Justesen, N., Holm, S., and Paulson, O. B. (1996) Changes in cerebral blood flow and carbohydrate metabolism during acute hyperketonemia. Am J Physiol 270:E746–51.

Hertz, L., A. C. Yu, et al. (2000). "Neuronal-astrocytic and cytosolic-mitochondrial metabolite trafficking during brain activation, hyperammonemia and energy deprivation." *Neurochem Int* 37(2–3):83–102.

Hoyer, S. (1998) Is sporadic Alzheimer disease the brain type of non-insulin dependent diabetes mellitus? A challenging hypothesis. JNeural Transm 105:415–22.

Hoyer, S. (1992) Oxidative energy metabolism in Alzheimer brain. Studies in early-onset and late-onset cases. Mol Chem Neuropathol 16:207–24.

Jolles, J., Bothmer, J., Markerink, M., and Ravid, R. (1992) Phosphatidylinositol kinase is reduced in Alzheimer's disease. J Neurochem 58:2326–9.

Kolanowski, J., Young, J. B., and Landsberg L. (1994) Stimulatory influence of D $(-)_3$-hydroxybutyrate feeding on sympathetic nervous system activity in the rat. Metabolism 43:180–5.

Klivenyi, P., Ferrante, R. J., Matthews, R. T., Bogdanov, M. B., Klein, A. M. Andreassen, O. A., Mueller, G., Wermer, M., Kaddurah-Daouk, R., and Beal, M. F. (1999) Neuroprotective effects of creatine in a transgenic animal model of amyotrophic lateral sclerosis. Nat. Med. 5:347–50.

Koo, E. H., Lansbury, P. T., Jr., and Kelly, J. W. (1999) Amyloid diseases: abnormal protein aggregation in neurodegeneration. Proc Natl Acad Sci USA. 96:9989–90.

Knouff, C., Hinsdale, M. E., Mezdour, H., Altenburg, M. K., Watanabe, M., Quarfordt, S. H., Sullivan, P. M., and Maeda, N. (1999) Apo E structure determines VLDL clearance and atherosclerosis risk in mice. J Clin Invest 103:1579–86.

Lannert, H., and Hoyer, S. (1998) Intracerebroventricular administration of streptozotocin causes long-term diminutions in learning and memory abilities and in cerebral energy metabolism in adult rats. Behav Neurosci 112:199–208.

Loktionov A., Vorster H., O'Neill I. K., Nell T., Bingham S. A., Runswick S. A., Cummings J. H. (1999) Apolipoprotein E and methylenetetrahydrofolate reductase genetic polymorphisms in relation to other risk factors for cardiovascular disease in UK Caucasians and Black South Africans. Atherosclerosis 145:125–35.

Mattson, M. P. (1998). Experimental models of Alzheimer's Disease. Science and Medicine March/April: 16–25.

McKhann, G., Drachman, D., Folstein, M., Katzman, R., Price, D., and Stadlan, E. M. (1984). Clinical diagnosis of Alzheimer's disease: report of the NINCDS-ADRDA Work Group under the auspices of Department of Health and Human Services Task Force on Alzheimer's Disease. Neurology 34:939–44.

Meier-Ruge, W., Bertoni-Freddari, C., and Iwangoff, P. (1994) Changes in brain glucose metabolism as a key to the pathogenesis of Alzheimer's disease. Gerontology 40:246–52.

Messier, C., and Gagnon, M. (1996) Glucose regulation and cognitive functions: relation to Alzheimer's disease and diabetes. Behav Brain Res 75:1–11.

Neve, R. L., and Robakis, N. K. (1998) Alzheimer's disease: a re-examination of the amyloid hypothesis. Trends Neurosci 21:15–9.

Nishimura, M., Yu, G., and St George-Hyslop, P. H. (1999) Biology of presenilins as causative molecules for Alzheimer disease. Clin Genet 55:219–25.

Odle, J. (1997) New insights into the utilization of medium-chain triglycerides by the neonate: Observations from a pig model. J Nutr. 127:1061–7.

Reiman, E. M., Caselli, R. J., Yun, L. S., Chen, K., Bandy, D., Minoshima, S., Thibodeau, S. N., and Osborne, D. (1996) Preclinical evidence of Alzheimer's disease in persons homozygous for the epsilon 4 allele for apolipoprotein E. N Engl J Med 334:752–8.

Osuntokun B. O., Sahota A., Ogunniyi A. O., Gureje O., Baiyewu O., Adeyinka A., Oluwole S. O., Komolafe O., Hall K. S., Unverzagt F. W., et al (1995) Lack of an association between apolipoprotein E epsilon 4 and Alzheimer's disease in elderly Nigerians. Ann Neurol 38:463–5.

Roheim P. S., Carey M., Forte T., and Vega G. L. (1979) Apolipoproteins in human cerebrospinal fluid. Proc Natl Acad Sci USA 76:4646–9.

Schoonjans, K., J. Peinado-Onsurbe, et al. (1999). "3-Hydroxy-3-methylglutaryl CoA reductase inhibitors reduce serum triglyceride levels through modulation of apolipoprotein C-III and lipoprotein lipase." FEBS Lett 452(3):160–4.

Selkoe, D. J. (1994) Alzheimer's Disease: A central role for amyloid. J. Neruopathol. Exp. Neruol. 53:438–447.

Selkoe, D. J., (1999) Translating cell biology into therapeutic advances in Alzheimer's disease. Nature 399:A23–31.

Simpson, I. A., and Davies, P. (1994) Reduced glucose transporter concentrations in brains of patients with Alzheimer's disease: Ann Neurol 36:800–1.

Staels, B., J. Dallongeville, et al. (1998). "Mechanism of action of fibrates on lipid and lipoprotein metabolism." *Circulation* 98(19):2088–93.

Swaab, D. F., Lucassen, P. J., Salehi, A., Scherder, E. J., van Someren, E. J., and Verwer, R. W. (1998) Reduced neuronal activity and reactivation in Alzheimer's disease. Prog Brain Res 117:343–77.

Veech, Richard WO 98/41200. Sep. 24, 1998. Therapeutic Compositions

Veech, Richard WO 98/41201. Sep. 24, 1998. Therapeutic Compositions

Veech, Richard WO 00/15216. Mar. 23, 2000. Therapeutic Compositions (II)

Veneman, T., Mitrakou, A., Mokan, M., Cryer, P., and Gerich, J. (1994) Effect of hyperketonemia and hyperlacticacidemia on symptoms, cognitive dysfunction, and counterregulatory hormone responses during hypoglycemia in normal humans. Diabetes 43:1311–7.

Zekraoui L., Lagarde J. P., Raisonnier A., Gerard N., Aouizerate A., Lucotte G. (1997) High frequency of the apolipoprotein E*4 allele in African pygmies and most of the African populations in sub-Saharan Africa. Hum Biol 69:575–81.

Zubenko, G. S., Stiffler, J. S., Hughes, H. B., and Martinez, A. J. (1999) Reductions in brain phosphatidylinositol kinase activities in Alzheimer's disease. Biol Psychiatry 45:731–6.

EXAMPLES

The following examples are offered by way of illustration and not by way of limitation.

Example 1

Nutritional Drink

Nutritional drinks are prepared using the following ingredients: emulsified MCT 100 g/drink, L-carnitine 1 gram/drink, mix of daily vitamins at recommended daily levels, and a variety of flavorings.

Example 2

Additional Formulations

Additional formulations can be in the form of Ready to Drink Beverages, Powdered Beverages, Nutritional drinks, Food Bars, and the like. Formulations for such are clear to those skilled in the art.

A. Ready to Drink Beverage Ready to Drink Beverages are prepared using the following ingredients: emulsified MCT 5–100 g/drink, L-carnitine 250–1000 mg/drink, and a variety of flavorings and other ingredients used to increased palatability, stability, etc.

B. Powdered Beverages MCT may be prepared in a dried form, useful for food bars and powdered beverage preparations. A powdered beverage may be formed from the following components: dried emulsified MCT 10–50 g, L-carnitine 250–500 mg, sucrose 8–15 g, maltodextrin 1–5 g, flavorings 0–1 g.

C. Food bar A food bar would consist of: dried emulsified MCT 0.1–50 g, L-carnitine 250–500 mg, glycerin 1–5 g, corn syrup solids 5–25 g, cocoa 2–7 g, coating 15–25 g.

D. Gelatin Capsules Hard or soft gelatin capsules are prepared using the following ingredients: MCT 0.1–1000 mg/capsule, L-carnitine 250–500 mg/capsule, Starch, NF 0–600 mg/capsule; Starch flowable powder 0–600'mg/capsule; Silicone fluid 350 centistokes 0–20 mg/capsule. The ingredients are mixed, passed through a sieve, and filled into capsules.

E. Tablets Tablets are prepared using the following ingredients: MCT 0.1–1000 mg/tablet; L-carnitine 250–500 mg/tablet; Microcrystalline cellulose 20–300 mg/tablet; Starch 0–50 mg/tablet; Magnesium stearate or stearate acid 0–15 mg/tablet; Silicon dioxide, filmed 0–400 mg/tablet; silicon dioxide, colloidal 0–1 mg/tablet, and lactose 0–100 mg/tablet. The ingredients are blended and compressed to form tablets.

F. Suspensions Suspensions are prepared using the following ingredients: 0.1–1000 mg MCT; 250–500 mg L-carnitine; Sodium carboxymethyl cellulose 50–700 mg/5 ml; Sodium benzoate 0–10 mg/5 ml; Purified water 5 ml; and flavor and color agents as needed.

G. Parenteral Solutions A parenteral composition is prepared by stirring 1.5% by weight of MCT and L-carnitine in 10% by volume propylene glycol and water. The solution is made isotonic with sodium chloride and sterilized.

Example 3

Treating Alzheimer's Disease with Medium Chain Triglycerides

The purpose of this study was to explore whether hyperketonemia improves cognitive functioning in individuals with memory disorders. The goal of this trial was to test the hypothesis that sustained elevation of serum beta-hydroxybutyrate (BHB) levels through a large oral dose of medium chain triglycerides will improve memory and attention performances in individuals with Alzheimer's Disease and Mild Cognitive Impairment.

Participants

The sample consisted of 20 individuals with memory disorders recruited from Western Washington. Potential subjects were excluded if they had diabetes mellitus, hypoglycemia, major psychiatric disorders, or other major medical or neurological disorders such as hypertension, hypotension, cardiac problems, or COPD. In addition, patients were excluded from the study if they were taking medications with CNS effects, such as anti-psychotics, anti-anxiolytics, and anti-hypertensives. However, subjects were allowed to participate if they were taking anti-depressants. Four participants were taking anti-depressants at the time of the study.

Table 1 describes the demographics of the sample. Fifteen subjects met NINCIDS/ADRDA criteria for probable AD. The remaining 5 subjects were diagnosed with Mild Cognitive Impairment, believed to be a prodromal phase of AD. Participants ranged in age from 61 to 84 years of age (mean=74.7), and 25% of the sample was female. The sample was well educated with an average of 13.3 years of education. Ninety percent of the sample was Caucasian. Two non-Caucasian subjects were identified as African-American and American Indian. Participants were typically in the mild to moderate stages of dementia. The mean baseline MMSE was 22.2. Forty-seven percent of the participants had at least one apoE E-4 allele.

TABLE 1

Sample Demographics and Medical Information

| Variable | Mean | SD |
| --- | --- | --- |
| Age | 74.7 | 6.7 |
| Education | 13.3 | 3.25 |
| BMI | 26.0 | 3.7 |
| MMSE | 22.2 | 5.5 |

| | n | Sample % |
| --- | --- | --- |
| AD | 15 | 75 |
| MCI | 5 | 25 |
| Female | 5 | 25 |
| E4+ | 10/19 | 53 |
| Non-Caucasian | 2 | 10 |

Note:
SD = Standard Deviation,
BMI = Body Mass Index,
MMSE = Mini-Mental State Examination,
E4+ = Subjects with at least one apoE E4 allele Procedures Subjects were recruited through medical clinics, senior centers, and ads in newspapers. Prospective subjects' medical histories and cognitive complaints were telephone screened by research nurses. Individuals were then referred to the Memory Disorders Clinic at the VA Puget Sound Health Care System (VAPSHCS) for clinical and/or neuropsychological evaluation. Routine laboratory assays and EKGs were completed to assist in diagnosis and determination of research inclusion.

The study was conducted with a randomized, double-blind placebo controlled, crossover design. Initially, subjects were asked to come to the VAPSHCS for three visits. During each visit, subjects received one of two conditions in a randomized order: emulsified long chain triglycerides as a placebo (232 ml of heavy whipping cream) or medium chain triglycerides (MCT; 40 ml). NeoBee 895 (Stepan, Inc.) was used for MCTs. MCT were blended with 152 ml of heavy whipping cream. Vanilla and non-caloric sweetener were added to the drink for taste.

Subjects arrived in the morning after a 12-hour fast and blood was drawn to determine BHB levels and apoE genotyping (first visit only). Subjects then consumed the blended test sample described above. About ninety minutes later, a second blood draw occurred and a 30-minute cognitive testing session ensued. A final blood draw was then completed. Study visits were conducted at least one week apart, and not more than four weeks apart.

Neuropsychological Measures

Neuropsychological testing was performed by trained psychometrists using standardized procedures. A picture naming task, designed as a warm-up test, was completed at the beginning of the 30-minute test battery to reduce subject anxiety. The cognitive protocol included paragraph recall, the Stroop Color Word Interference Task, the Alzheimer's Disease Assessment Scale-Cognitive Subscale (ADAS-cog), and the Mini-Mental State Examination (MMSE).

The Logical Memory subtest of the Wechsler Memory Scale-III was used as the model for the paragraph recall test. Subjects heard brief narratives containing 25 bits of information. They were asked to recall as much information as possible, both immediately after hearing the story and again after a 10 minute delay.

The Stroop Color Word Interference Task is a test of selective attention. The first two conditions require speeded reading of color words and speeded naming of colored blocks on a page. In the third condition, color names are printed in discordant ink colors and subjects are asked to state the color of the ink while inhibiting reading of the color words. Total reading time was recorded.

The ADAS-cog is a mental status test designed specifically to rate the cognitive functioning of patients with Alzheimer's Disease. Scores range from 1 to 70 with higher scores indicating increased impairment.

The MMSE is a brief mental status test. Scores range from 0 to 30 with lower scores indicating increased impairment.

BHB Assays

Blood was processed immediately on the day of each subject's visit. Blood serum samples were kept in a $-70°$ C. freezer until completion of the study. BHB levels were determined using a beta-hydroxybutyrate diagnostic kit (Sigma Diagnostics, Inc.). All samples were included in the assays and the lab was blinded to treatment conditions.

Results

Treatment Effects on BHB Levels For BHB levels, a repeated measures ANCOVA was conducted with the apoE genotype as the independent factor (E4+vs. E4−), and condition (treatment vs placebo) and time of blood draw (0, 90 min, and 120 min) as repeated factors and BMI as a covariate. BHB levels increased significantly with treatment ($F[1, 15]=5.16$, $p<0.039$), and there was a significant difference in BHB levels at different time points ($F[2, 14]=5.22$, $p<0.01$). Significant increases in BHB levels were observed 90-minutes after treatment ($p=0.007$). In addition, there was a significant interaction between E4 status and time of blood draw ($F[2, 14]=3.76$, $p=0.036$). Contrasts revealed that the BHB levels for E4+subjects continued to rise between the 90-minute and 120-minute blood draws in the treatment condition, while the BHB levels of E4-subjects held constant ($p<0.003$). Table 2 lists the BHB means and standard deviations for each E4 group.

TABLE 2

Mean BHB Values by Treatment Condition and apoE E4 Status

| E4 Status | Baseline Mean | SD | 90' Mean | SD | 120' Mean | SD |
|---|---|---|---|---|---|---|
| Placebo | | | | | | |
| E4− | .04648 | .03565 | .07525 | .04780 | .09241 | .05803 |
| E4+ | .14013 | .17946 | .15589 | .16760 | .18549 | .18405 |
| MCT Treatment | | | | | | |
| E4− | .04150 | .02375 | .53784 | .31535 | .51515 | .25437 |
| E4+ | .09504 | .08286 | .43022 | .18648 | .74142 | .37714 |

Figure 2:
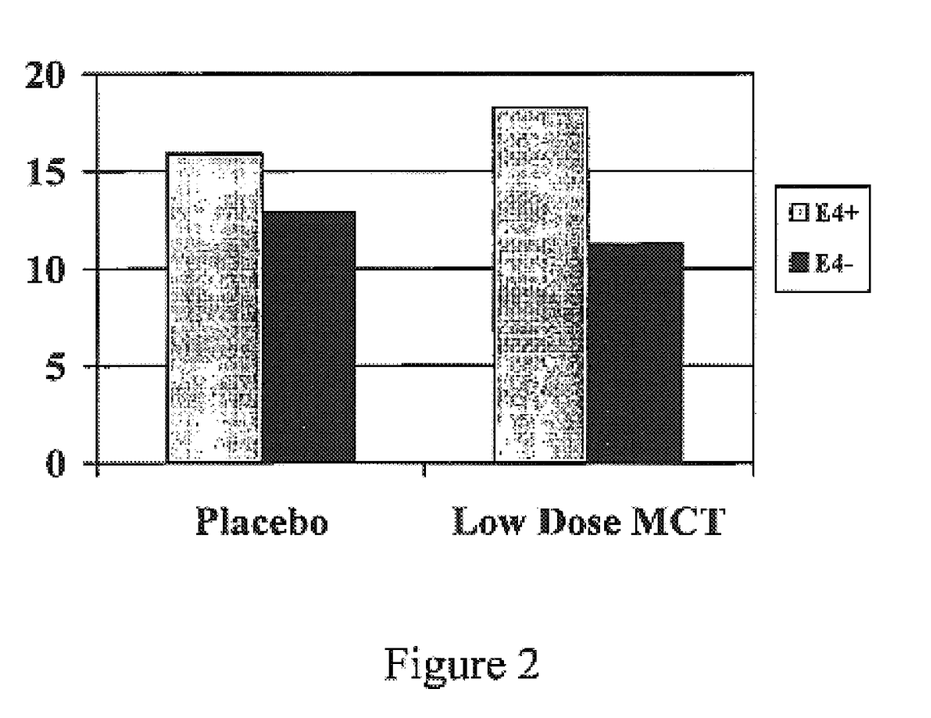
FIG. 2 shows the results of treatment on cognitiye performance for apoE4+ and apoE4-patients.

Note:
90' = Values drawn 90 minutes after treatment;
120' = Values drawn 120 minutes after treatment Treatment Effects on Cognitive Performance Repeated measures ANCOVAs were conducted with the apoE E4 allele as the independent factor (E4+vs. E4−) and condition (treatment vs placebo) as the repeated factor, BHB levels at the time of cognitive testing as a covariate, and cognitive measures as the dependent variables. For the ADAS-cog, subjects without the apoE-E4 allele showed improvement following MCT administration, whereas E4+subjects showed ADAS-cog Total Scores (lower scores indicate better performance) with slightly worse performance (Table 2). This pattern resulted in a significant condition by E4 interaction ($F[2, 14]=13.63$, $p=0.002$). (see FIG. 2).

The repeated measures ANCOVA with paragraph recall as the dependent measure revealed a trend interaction between the effects of treatment and BHB values measured just before testing ($F[1,14]=4.38$, $p=0.055$). Subjects whose BHB levels were higher showed improved paragraph recall with MCT administration.

What is claimed is:

1. A method of treating dementia of Alzheimer's type, comprising
   a) providing a patient having Alzheimer's disease, and having a diet wherein carbohydrate intake is not restricted, and
   b) administering an effective amount of medium chain triglycendes to said patient, wherein the medium chain triglycerides comprise fatty acid residues containing six to ten carbons esterified to a glycerol backbone, and wherein said medium chain triglycerides are administered at a dose of about 0.5 g/kg/day to about 10 g/kg/day.

2. The method of claim 1, wherein said administration is oral.

3. The method of claim 1, wherein said administration is intravenous.

4. The method of claim 1, wherein said medium chain triglycerides are emulsified.

* * * * *